(12) United States Patent
Gutierrez et al.

(10) Patent No.: US 10,564,089 B2
(45) Date of Patent: Feb. 18, 2020

(54) CROSS-INSTRUMENT METHOD AND SYSTEM FOR CELL POPULATION DISCRIMINATION

(71) Applicant: Beckman Coulter, Inc., Brea, CA (US)

(72) Inventors: William H. Gutierrez, Miami, FL (US); Cheng Qian, Miami, FL (US); John S. Riley, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 670 days.

(21) Appl. No.: 15/263,133

(22) Filed: Sep. 12, 2016

(65) Prior Publication Data

US 2017/0010204 A1    Jan. 12, 2017

Related U.S. Application Data

(62) Division of application No. 12/397,650, filed on Mar. 4, 2009, now Pat. No. 9,464,978.

(51) Int. Cl.
| | | |
|---|---|---|
| G01N 15/14 | (2006.01) | |
| G01N 15/12 | (2006.01) | |
| G01N 15/00 | (2006.01) | |
| G01N 15/10 | (2006.01) | |

(52) U.S. Cl.
CPC ......... *G01N 15/1429* (2013.01); *G01N 15/12* (2013.01); *G01N 15/1209* (2013.01); *G01N 15/147* (2013.01); *G01N 2015/008* (2013.01); *G01N 2015/0073* (2013.01); *G01N 2015/1037* (2013.01); *G01N 2015/1497* (2013.01)

(58) Field of Classification Search
None
See application file for complete search history.

(56) References Cited

U.S. PATENT DOCUMENTS

| | | |
|---|---|---|
| 4,599,307 A | 7/1986 | Saunders et al. |
| 4,987,086 A | 1/1991 | Brosnan et al. |
| 5,064,616 A | 11/1991 | Brosnan et al. |
| 5,234,816 A | 8/1993 | Terstappen |
| 5,631,165 A | 5/1997 | Chupp et al. |
| 5,631,730 A | 5/1997 | Chupp et al. |
| 5,656,499 A | 8/1997 | Chupp et al. |
| 5,692,220 A | 11/1997 | Diamond et al. |
| 5,812,419 A | 9/1998 | Chupp et al. |
| 5,939,326 A | 8/1999 | Chupp et al. |
| 6,228,652 B1 | 5/2001 | Rodriguez et al. |
| 9,464,978 B2 | 10/2016 | Gutierrez et al. |
| 9,802,727 B2 | 10/2017 | Cooper |
| 2007/0072300 A1 | 3/2007 | Simon-Lopez |
| 2010/0228491 A1 | 9/2010 | Gutierrez et al. |

FOREIGN PATENT DOCUMENTS

| | | | |
|---|---|---|---|
| EP | 0559208 A1 | 9/1993 | |
| EP | 1770387 A2 | 4/2007 | |
| EP | 2404156 A1 | 1/2012 | |
| JP | 60076666 A | 5/1985 | |
| JP | H09508703 A | 9/1997 | |
| JP | H09508705 A | 9/1997 | |
| JP | 2002503333 A | 1/2002 | |
| JP | 2003510557 A | 3/2003 | |
| JP | 2007101539 A | 4/2007 | |
| JP | 2007515623 A | 6/2007 | |
| JP | 2009511861 A | 3/2009 | |
| JP | 2012519848 A | 8/2012 | |
| JP | 5636381 B2 | 10/2014 | |
| WO | WO/1998/002727 | * | 7/1998 |
| WO | WO-2005043113 A2 | 5/2005 | |
| WO | WO-2010101751 A1 | 9/2010 | |

OTHER PUBLICATIONS

"U.S. Appl. No. 12/397,650, Advisory Action dated Oct. 7, 2015", 4 pgs.
"U.S. Appl. No. 12/397,650, Examiner Interview Summary dated Aug. 1, 2012", 4 pgs.
"U.S. Appl. No. 12/397,650, Examiner Interview Summary dated Sep. 4, 2015", 3 pgs.
"U.S. Appl. No. 12/397,650, Final Office Action dated Apr. 12, 2012", 8 pgs.
"U.S. Appl. No. 12/397,650, Final Office Action dated May 22, 2015", 18 pgs.
"U.S. Appl. No. 12/397,650, Non Final Office Action dated Oct. 4, 2011", 8 pgs.
"U.S. Appl. No. 12/397,650, Non Final Office Action dated Nov. 6, 2014", 13 pgs.
"U.S. Appl. No. 12/397,650, Notice of Allowance dated Jun. 6, 2016", 9 pgs.
"U.S. Appl. No. 12/397,650, Response filed Feb. 6, 2015 to Non Final Office Action dated Nov. 6, 2014", 10 pgs.
"U.S. Appl. No. 12/397,650, Response filed Feb. 17, 2012 to Non Final Office Action dated Oct. 4, 2011", 10 pgs.
"U.S. Appl. No. 12/397,650, Response filed Jul. 29, 2011 to Restriction Requirement dated Jul. 7, 2011", 8 pgs.
"U.S. Appl. No. 12/397,650, Response filed Sep. 22, 2015 to Final Office Action dated May 22, 2015", 12 pgs.
"U.S. Appl. No. 12/397,650, Response filed Oct. 11, 2012 to Final Office Action dated Apr. 12, 2012", 12 pgs.

(Continued)

*Primary Examiner* — Michael L Borin
(74) *Attorney, Agent, or Firm* — Schwegman Lundberg & Woessner, P.A.

(57) ABSTRACT

The present invention provides methods and systems to combine the capabilities of a hematology analyzer with those of a flow cytometer to yield a far more powerful analytical system than either device alone. In one embodiment, a method of analyzing a cell sample includes receiving a first data generated by an analysis of a first aliquot of the sample on a first particle analyzer having a fluorescence measurement device such as a flow cytometer, detecting at least one unresolved cell population in the first data, and accessing a second data stored on a storage device wherein the second data was previously generated by interrogating a second aliquot of the sample using at least one of a cell volume measurement device and a cell conductivity measurement device in a second particle analyzer such as a hematology analyzer. The unresolved cell population in the first data is then resolved using the second data. Corresponding system embodiments are also disclosed.

13 Claims, 14 Drawing Sheets

(56) References Cited

OTHER PUBLICATIONS

"U.S. Appl. No. 12/397,650, Response filed Nov. 23, 2015 to Advisory Action dated Oct. 7, 2015", 13 pgs.
"U.S. Appl. No. 12/397,650, Restriction Requirement dated Jul. 7, 2011", 6 pgs.
"International Application Serial No. PCT/US2010/025247, International Search Report dated May 3, 2010", 4 pgs.
Fest, Thierry, "Flow Cytometry—the Key to Automated, Objective Validation of Abnormal Samples", [Online] retrieved from the Internet: http://clionline.com/index:php?id=2350, (Feb. 3, 2009), 1-5.
Jean-Luc, Faucher, et al., ""6 Markers/5 Colors" Extended White Blood Cell Differential by Flow Cytometry", Cytometry Part A, 71A, (2007), 934-944.
Sven, Bjornsson, et al., "Total Nucleated Cell Differential for Blood and Bone Marrow Using a Single Tube in a Five-Color Flow Cytometer", Cytometry Part B (Clinical Cytometry) 74B, (2008), 91-103.
"European Application Serial No. 10706444.6, Communication Pursuant to Article 94(3) dated Nov. 9, 2016", 6 pgs.
"European Application Serial No. 10706444.6, Communication Pursuant to Article 94(3) dated Nov. 15, 2017", 6 pgs.
"European Application Serial No. 10706444.6, Intention to Grant dated Aug. 1, 2019", 49 pgs.
"European Application Serial No. 10706444.6, Response filed Apr. 27, 2012 to Communication Pursuant to Rules 161(1) and 162 EPC dated Oct. 17, 2011", 18 pgs.
"European Application Serial No. 10706444.6, Response filed May 19, 2017 to Communication Pursuant to Article 94(3) dated Nov. 9, 2016", 11 pgs.
"European Application Serial No. 10706444.6, Response filed Aug. 24, 2018 to Communication Pursuant to Article 94(3) dated Nov. 15, 2017", 13 pgs.
"International Application Serial No. PCT/US2010/025247, International Preliminary Report on Patentability dated Sep. 15, 2011", 9 pgs.
"International Application Serial No. PCT/US2010/025247, Written Opinion dated May 3, 2010", 7 pgs.
"Japanese Application Serial No. 2011-552985, Notification of Reasons for Rejection dated Sep. 9, 2013", w/ English Translation, 4 pgs.
"Japanese Application Serial No. 2011-552985, Response filed Jan. 8, 2014 to Notification of Reasons for Rejection dated Sep. 9, 2013", 18 pgs.

* cited by examiner

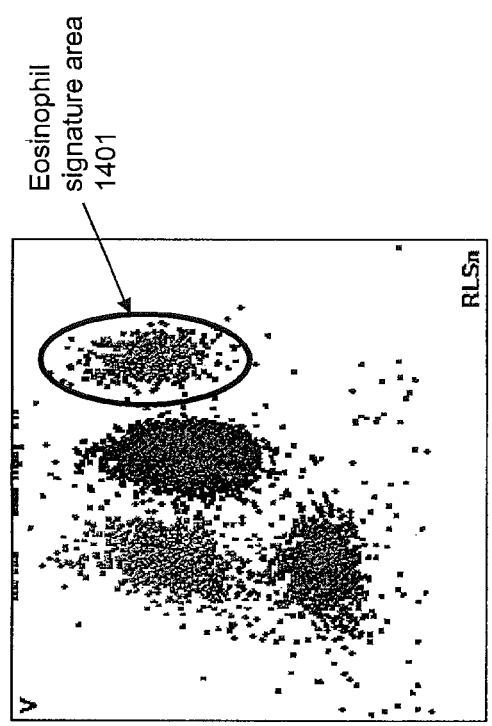

CROSS-INSTRUMENT METHOD AND SYSTEM FOR CELL POPULATION DISCRIMINATION

BACKGROUND OF THE INVENTION

This application is a divisional of U.S. patent application Ser. No. 12/397,650 filed on Mar. 4, 2009, now U.S. Pat. No. 9,464,978, the entire disclosure of which is incorporated by reference herein.

FIELD OF THE INVENTION

This invention relates in general to the analysis of particles using particle analyzers, and more particularly to using results obtained using a particle analyzer having a cell volume measurement device, a light scatter measurement device, or a cell conductivity measurement device, to further discriminate cell populations detected through a particle analyzer having a fluorescence measurement device.

BACKGROUND

In medical diagnostic facilities, efficient and accurate diagnosis of blood and other bodily fluids is of key importance. Increased accuracy and efficiencies in terms of costs as well as time associated with the analysis of each sample are sought. Such medical diagnostic facilities employ at least two types of particle analyzers: hematology analyzers and flow cytometers. Hematology analyzers and flow cytometers measure and differentiate blood cells by collecting and analyzing signals produced when the blood cells pass through a small aperture or measurement region that is monitored by one or more sensors.

Hematology analyzers, in general, use electrical impedance to classify and count red and white blood cells based on their size and/or volume. Electrical impedance analysis involves transmitting an electrical current through a measurement region in the flow cell of the particle analyzer. The impedance of the current (measured between two terminals across the measurement region of the flow cell, for example) changes in relation to the cells that pass through. This is also known as the Coulter principle. Hematology analyzers can also utilize one or more beams of light to measure light scatter and reflectance to classify cells based on properties including size and granularity. Example hematology analyzers include COULTER® LH 700 Series manufactured by Beckman Coulter, and XE-2100™ manufactured by Sysmex.

Flow cytometers measure cell characteristics using detected fluorescence characteristics of cells when the cells are combined with one or more known fluorochromes. Labeling of the cells with fluorochromes that bind with high specificity to one particular cell type, makes it is possible to measure the contents of the cells. Such a fluorescent tag can be either a fluorescence dye molecule with a high binding-specificity for the particular component to be measured, or a fluorescence-conjugated antibody. The light scatter and reflectance of the cells yield information on their size, shape, and structure. Flow cytometers are capable of rapid, quantitative, multi-parameter analysis of heterogeneous cell populations on a cell-by-cell basis. Example flow cytometers include FC 500 ™ manufactured by Beckman Coulter, and FACSCanto™ manufactured by Becton Dickinson.

In laboratory settings, hematology analyzers and flow cytometers each have their respective strengths. Hematology analyzers are considered workhorse analytic instruments in that they are designed to economically process many routine assays per hour. For example, hematology analysis is widely used for such tests as complete blood count (CBC), reticulocyte analysis, and white blood cell differentials. Flow cytometers are used for additional tests that are generally costlier and more time consuming than those performed by hematology analyzers. Flow cytometry is particularly useful in the diagnosis and treatment of diseases such as leukemia, HIV/AIDS, and lymphomas, because it allows the monitoring of the proportion of a particular type of cell in the blood sample.

However, although hematology analyzers and flow cytometers are powerful analytical tools in and of their own accord, they each have limitations in the laboratory environment. Hematology analyzers cannot perform tests that detect proportion of cell types through the use of antibodies or fluorochromes. Flow cytometers are slow relative to hematology analyzers and require numerous costly antibodies and fluorochromes. Therefore, the need to harness the capabilities of both instruments to make a more robust particle analyzer system for medical diagnosis cannot be understated.

Presently, some blood samples are analyzed on a hematology analyzer as well as a flow cytometer. A typical scenario in a medical diagnostic facility can be the running of several hundred samples a day though a hematology analyzer, and then, for various reasons, having some of those samples further analyzed by a flow cytometer. For example, a flag generated by the hematology analyzer may represent the detection of a high white blood cell count. An example of a standing order to perform follow-on analysis in a flow cytometer may be for samples suspected of leukemia. Alternatively, and in some cases, samples flagged by the hematology analyzer can be further analyzed by a highly trained technician. The technician, typically, would prepare slides that are then manually examined. Also, in many cases, even having analyzed the sample through a flow cytometer, certain cell populations remain unresolved. In such cases, manual intervention is required by highly trained technicians to resolve the two separate sets of results generated by the hematology analyzer and the flow cytometer. Manual intervention by technologists is also costly, and introduces complications due to the potential for human error.

Some analytic instruments, such as the SAPPHIRE manufactured by Abbott Laboratories, combine aspects of a hematology analyzer with that of a flow cytometer. See, also, U.S. Pat. Nos. 5,939,326, 5,656,499, and 5,631,165. It is understood that the SAPPHIRE uses hematology analysis to determine characteristics such as total cell counts of cell types including cell types discovered in flow cytometry analysis. It is also understood that, at any given time, the SAPPHIRE can only operate either in the hematology analysis mode or in the flow cytometry mode. Having the instrument operate only in one mode at a time, for example, limits some of the advantages, such as speed and efficiency, of combining a hematology analyzer and flow cytometer.

Therefore, improved methods and systems for effectively leveraging capabilities of different types of particle analyzers are needed.

BRIEF SUMMARY OF THE INVENTION

Substantial benefits can be obtained by automating the use of the full capabilities of a hematology analyzer as well as a flow cytometer in such a way as to reduce the need for manual intervention. The present invention provides methods and systems to combine the capabilities of a hematology analyzer with that of a flow cytometer to yield a far more powerful analytical system than either instrument alone. In one embodiment, a method of analyzing a cell suspension sample includes the steps of receiving a first data generated by an analysis of a first aliquot of the cell suspension sample on a first particle analyzer that has a fluorescence measurement device, detecting at least one unresolved cell population in the first data, accessing a second data stored on a storage device, and resolving the unresolved cell population using the second data. The second data was previously generated by interrogating a second aliquot of the same cell suspension sample using at least one of a cell volume measurement device and a cell conductivity measurement device in a second particle analyzer. The first and second particle analyzers, respectively, can be a flow cytometer and a hematology analyzer.

Another embodiment is a method for analyzing a cell suspension sample that includes the steps of, preparing a first aliquot of the cell suspension sample for analysis on a particle analyzer that has a fluorescence measurement device, interrogating the first aliquot using the fluorescence measurement device to generate a first data, and accessing a second data stored on a storage device where the second data was previously generated by interrogating a second aliquot of the cell suspension sample in a second particle analyzer using at least one of a cell volume measurement device and a cell conductivity measurement device. The unresolved cell population in the first data is then resolved using the second data to generate a resolved cell data. The resolved cell data can then be reported.

Yet another embodiment is a system for analysis of a cell suspension sample, including, a first particle analyzer configured to receive a first aliquot of the sample as input and to produce a first data using a fluorescence measurement device, a second particle analyzer configured to receive a second aliquot of said sample as input and to produce a second data using at least one of a cell volume measurement device and a cell conductivity measurement device, a storage device configured to receive the second data from the second particle analyzer, and a computer configured to receive the first data and the second data and to produce a resolved cell distribution where the first data includes at least one cell population that is not resolvable based only on the first data. A further embodiment includes a reporting device configured to receive the resolved cell distribution from the computer.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

FIG. 14 is a scatter plot of a eosinophil-positive sample of FIGS. 12 and 13 analyzed in a hematology analyzer.

Figure 1:
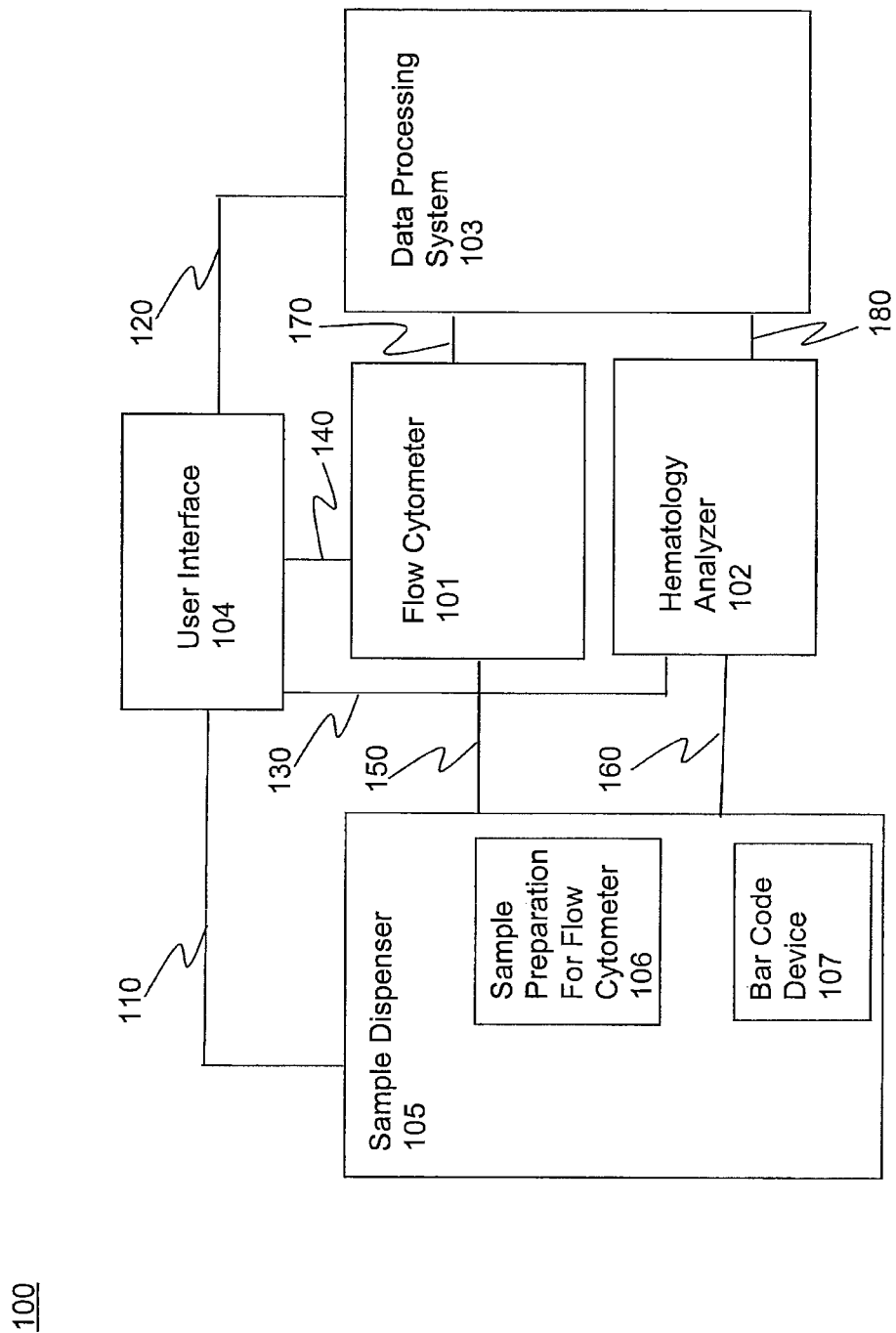
FIG. 1 illustrates a system according to an embodiment of the present invention.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION OF THE INVENTION

The present invention provides methods and systems to combine the capabilities of a hematology analyzer with those of a flow cytometer to yield a far more powerful analytical system than either instrument alone. While the present invention is described herein with reference to illustrative embodiments for particular applications, it should be understood that the invention is not limited thereto. Those skilled in the art with access to the teachings herein will recognize additional modifications, applications, and embodiments within the scope thereof and additional fields in which the invention would be of significant utility.

Overview

Embodiments of the present invention combine the analytical capabilities of a hematology analyzer with those of a flow cytometer to yield methods and systems for using results obtained from one type of analysis to interpret the results obtained from the other type of analysis. For example, an embodiment of the present invention uses the results of hematology analysis to further interpret and discriminate cell populations discovered through flow cytometric analysis of the same blood sample. Such cross-instrument analysis can be highly beneficial in reducing the level of manual labor involved in interpreting test results when both types of analysis is done. The synergy achieved drastically reduces the time required for complex analysis using both types of analysis, and lowers the costs of such analysis. The synergistic results achieved by sharing data between a hematology analyzer and a flow cytometer according to the systems and methods of the present invention are significant.

As an example, when analyzing a Myeloblast-positive blood sample, most hematology analyzers are only capable of displaying non-numeric suspect messages because they do not have the capability to perform Myeloblast enumeration. On the other hand, a flow cytometer using a particular combination of antibodies that does not directly mark Myeloblasts, may generate inaccurate Myeloblast information if the sample contains Plasmocytes, because Plasmocytes appear in the same location as Myeloblasts in scatter plots. Therefore, Myeloblast cell populations in flow cytometric data, in many cases, may be considered inconclusive or unresolved. However, results generated from a hematology analyzer for a Myeloblast-positive sample show distinctly different features in one or more other cell populations than for a Plasmocyte-positive sample. Embodiments of this invention, for example, when analyzing a flow cytometry result in which it cannot be resolved whether a particular population is Myeloblasts or Plasmocytes, can automatically examine the hematology analysis results generated for the same blood sample to make a more complete determination. Further details of this example embodiment is provided below with respect to FIGS. 5-8. Other applications, include, but are not limited to, using hematology results to distinguish between T-Blast cell populations and Basophil populations, or Eosinophils and immature Granulocyte populations in flow cytometer results.

Using conventional methods for resolving cell populations typically requires either the manual examination of a range of test result data by a technician, or the performance of additional testing on the same sample, such as reflex testing. Manual intervention to interpret results is costly and often error prone. Performing additional tests on the same sample incurs additional time, disrupts the testing pipeline, and can also substantially increase associated costs by introducing, for example, additional monoclonal antibodies and/or fluorochromes that can specifically mark each desired cell population for each test. Embodiments of the present invention, as indicated from the example applications described herein, enable expanding vital testing capabilities without increasing costs by enabling the automatic leveraging of cross-instrument data in the interpretation of results.

While enabling the combination of the capabilities of both instruments, the present invention also maintains the hematology analyzer and the flow cytometer as separate and independent particle analyzers. Maintaining the particle analyzers separately and independently enables the use of the combined system, for example, to run batches of blood samples in purely a high throughput hematology analyzer mode, purely a flow cytometer mode, or a combined mode where the results of one particle analyzer can be used to enhance and/or interpret the results obtained through the other particle analyzer. Even in the combined mode, embodiments of the present invention enables each of the two streams of analysis to operate at its own pace, thereby ensuring that, particularly in large scale batch testing environments, the substantially more expeditious hematology analysis process is not delayed due to flow cytometric analysis requirements.

Exemplary environments in which this invention can be practiced include hematology analyzers and flow cytometers, such as Beckman Coulter's Gen S™ System and FC 500™ respectively. The Gen S™ System, for example, is a hematology analyzer that uses the Coulter proprietary Volume, Conductivity, and Scatter (VCS) technology to probe hydrodynamically focused cells within a flow cell. VCS uses three independent measurement devices that work in concert with each other to probe cells: a cell volume measurement device using a low frequency direct current power source to measure volume; a cell conductivity measurement device using a high frequency power source to measure conductivity, and a laser light source to measure light scatter. The volume measurement is performed using the Coulter Principle of electrical impedance to physically measure the volume that the entire cell displaces in an isotonic diluent. This method accurately sizes all cell types regardless of their orientation in the light path. Alternating current in the radio frequency (RF) range short circuits the bipolar lipid layer of a cell's membrane, allowing the energy to penetrate the cell. This powerful probe is used to collect information about cell size and internal structure, including chemical composition and nuclear volume. A laser and multiple-angle light scatter sensors or detectors provide information about a cell's internal structure, granularity, and surface morphology.

In addition, VCS instruments use the highly accurate DC measurement of volume, to obtain other measurements that are adjusted for cell size from conductivity and scatter. For example, the conductivity signal can be corrected so that it is no longer affected by cell size and is therefore more accurately representative of the internal structure of the cell. Separating cells of similar size based on different compositions allows distinguishing cell populations like Variant Lymphocytes from normal Lymphs. Also, by adjusting light scatter signals to eliminate the size component (the adjusted scatter is often referred to as the rotated light scatter in VCS documents) the optimum scatter angle for each cell type can be monitored. This allows VCS technology to accurately separate what would normally be mixed cell types, such as Neutrophils and Eosinophils, into distinct clusters without mathematical manipulation. It also enhances the separation between non-granular cell types. U.S. Pat. No. 5,616,501 (to Rodriguez et. al), which is hereby incorporated by reference in its entirety, contains a detailed description of a particle analyzer and the use of VCS technology. It should be noted, however, that the teachings in this disclosure are not limited to devices using VCS technology. For example, the teachings herein are also applicable to Multisizer™ 3 Coulter Counter®, a particle analyzer with numerous applications in addition to biological sample analysis. The FC 500™ is a flow cytometer that, in addition to measurement devices of the VCS technology, also includes a fluorescence measurement device for optical analysis based on fluorescence characteristics of a selected set of fluorochromes. Other applicable measurements performed by known hematology analyzers and flow cytometers are well known to persons having ordinary skill in the relevant arts.

System for Cross-Instrument Pattern Analysis for Cell Population Discrimination

For ease of description, the system combining a flow cytometer and a hematology analyzer according to an embodiment of the present invention is herein referred to as the "Flow-H." FIG. 1 illustrates components of Flow-H 100. FIG. 1 is for illustrative purposes only, and it should be understood that systems according to embodiments of the present invention can include more or less components, different components, and/or different designs than shown in FIG. 1. Flow-H 100 includes a flow cytometer 101, hematology analyzer 102, a data processing system 103, a user interface 104, and a sample dispenser 105. Flow cytometer 101 can be a conventional flow cytometer such as the FC 500™, or a custom flow cytometer created specifically for the Flow-H. Hematology analyzer 102 can be a conventional hematology analyzer such as the Gen S™, or a custom hematology analyzer created specifically for carrying out the present invention.

Data processing system 103 can include a personal computer, server computer, mainframe computer, laptop computer, or any other device capable of implementing hardware and software instructions to receive data from flow cytometer 101 and hematology analyzer 102, and to thereby process that data according to the teachings of this disclosure. Data processing system 103 can include one or more communicatively coupled processing platforms. For example, aspects of data processing system 103 that exclusively include flow cytometric processing can reside in flow cytometer 101. Aspects of data processing system 103 that exclusively include hematology analyzer processing can reside in hematology analyzer 102. Moreover, aspects of data processing system 103 that combine flow cytometric processing and hematology analyzer processing can reside in a separate processing platform coupled to flow cytometer 101 and hematology analyzer 102. In one embodiment, data processing system 103 includes a conventional lab information system, such as the DL2000 DATA MANAGER from Beckman Coulter, which is used in medical diagnostic facilities. Data processing system 103 is further described below with respect to FIG. 2.

User interface 104 can include one or more displays, storage devices, output devices, and input devices. User interface 104 can be communicatively coupled to one or more components of Flow-H 100, such as, flow cytometer 101, hematology analyzer 102, data processing system 103, and sample dispenser 105. A display included in user interface 104 can receive and display data such as, for example, particle analysis results from the flow cytometer 101 and hematology analyzer 102 either directly or through data processing system 103. One or more input devices of user interface 104, such as, for example, keyboard or mouse, can enable an operator to configure the operation of Flow-H 100 or one of its components, to issue commands to direct operation of Flow-H 100, to provide input, and to provide the output generated by Flow-H 100. One or more storage devices in user interface 104 can include persistent storage devices such as hard disk, digital video disk (DVD), flash disk, and the like. One or more storage devices in user interface 104 can also include memories such as static random access memory (SRAM), dynamic random access memories (DRAM), and the like. Storage devices can be used to store commands, scripts, profiles, rules, and software programs, and the like, for the operation of Flow-H 100 or one or more of its components. One or more of the storage devices in user interface 104 can also be used to store results obtained from analysis of particle samples in flow cytometer 101, hematology analyzer 102, and/or the combined analysis of such results.

Sample dispenser 105 can be optionally included in Flow-H 100, according to embodiments of the present invention. Sample dispenser 105 enhances the automation of particle sample analysis using Flow-H 100 by enabling the operator to queue multiple samples for analysis, such that Flow-H 100 can process each of the queued samples automatically without further manual intervention. Sample dispenser 105 can include devices (not shown) for loading of samples, for mixing of samples in preparation for analysis, and for distributing the samples to flow cytometer 101 and to hematology analyzer 102 as configured. Sample dispenser 105 can include a flow sample preparation device 106 that performs any additional processing (such as the addition of fluorochromes or antibodies) and/or incubation of samples prior to analysis in flow cytometer 101. Sample dispenser 105 can also include a bar code device 107 that enables bar coding capability and/or bar code reading capability such that samples can be correctly processed and matched within Flow-H 100. For example, a bar code can be used to identify each unique sample, and each aliquot of that unique sample, such that results of analysis from hematology analyzer 102 can be matched with the corresponding results from flow cytometer 101. Sample dispensers are known in the art.

Interface 110 between sample dispenser 105 and user interface 110 enables sample dispenser 105 to receive configuration commands and to display feedback such as error conditions to user interface 104. Interface 120 between user interface 104 and data processing system 103 enables the data processing system to receive configuration information, profiles, rules, etc., from the user interface 104, and to provide feedback including analysis results to user interface 104. Interface 130 enables hematology analyzer 102 to receive configuration information from user interface 104, and to provide feedback to the user including results from analysis and/or error status indications. Interface 140 enables flow cytometer 101 to receive configuration information from user interface 104, and to provide feedback to the user including results from analysis and/or error status indications.

Interface 150 between sample dispenser 105 and flow cytometer 101 represents a mechanical interface that enables flow cytometer 101 to receive a cell suspension sample from sample dispenser 105. Interface 150 also represents a unidirectional or bidirectional interface between sample dispenser 105 and flow cytometer 101 for the flow of control information to coordinate the dispensing of samples. Likewise, interface 160 between sample dispenser 105 and hematology analyzer 102 represents a mechanical interface that enables hematology analyzer 102 to receive a cell suspension sample from sample dispenser 105. Interface 160 can also represent a unidirectional or bidirectional interface between sample dispenser 105 and hematology analyzer 102 for the flow of control information to coordinate the dispensing of samples. Interfaces 110, 120, 130, 140, 170, and 180, can include one or more communication mediums such as, peripheral component interconnect (PCI) bus, ethernet, or a wireless network such as IEEE 802.11, or the like. Likewise, interfaces 150 and 160 can also include one or more communication mediums such as peripheral component interconnect (PCI) bus, ethernet, or a wireless network such as IEEE 802.11, or the like, in addition to the mechanical interfaces utilized therein for sample dispensing.

Figure 2:
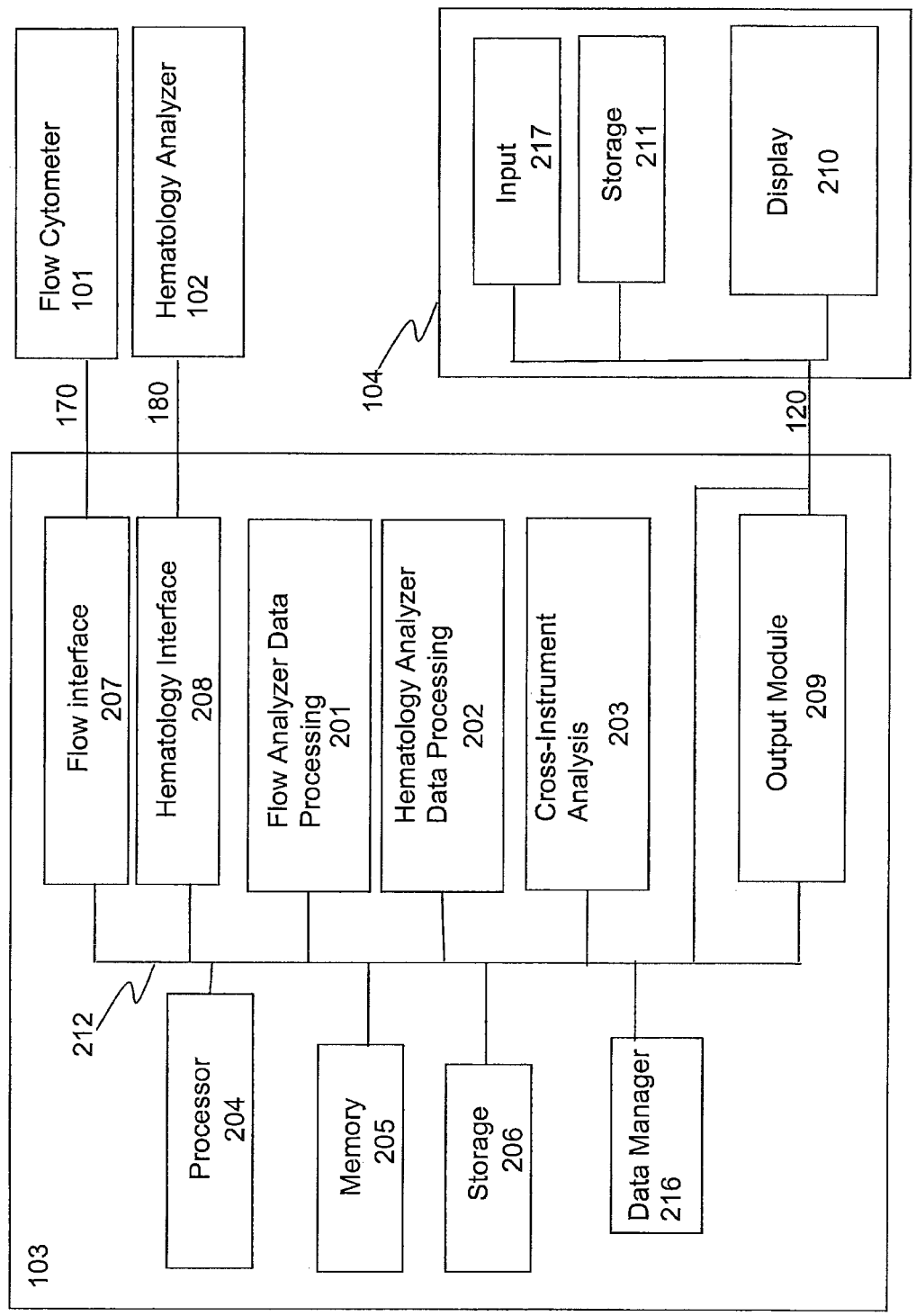
FIG. 2 illustrates the system of FIG. 1 in more detail, according to an embodiment of the present invention.

FIG. 2 illustrates data processing system 103 in more detail, according to an embodiment of the present invention. As described above, data processing system 103 is connected to flow cytometer 101, hematology analyzer 102, and user interface 104. User interface 104, can include devices including, but not limited to, one or more storage devices 211, one or more input devices 217, and one or more display devices 210. User interface 104 can be coupled to data processing system using an interface 120. Interfaces 170 and 180 couple data processing system 103 to flow cytometer 101 and hematology analyzer 102, respectively.

In certain embodiments, data processing system 103 includes at least one control processor 204, one or more memories 205, one or more persistent storage devices 206, a flow interface 207, a hematology interface 208, flow analyzer processing module 201, hematology analyzer data processing module 202, cross instrument analysis module 203, output module 209, a data manager 216, and a communication medium 212 interconnecting components of data processing system 103. One or more control processors 204 can include a special purpose computer, such as a programmed commercially available central processor units (CPU), or other processors such as digital signal processor (DSP), application specific integrated circuit (ASIC), or field programmable gate arrays (FPGA). The one or more control processors 204, as described above, can be located in one platform or multiple platforms including, for example, flow cytometer 101, hematology analyzer 102, data processing system 103, user interface 104, and/or sample dispenser 105. Each of one or more control processors 204 includes functionality to implement the logic instructions directing the operation of Flow-H 100, including, for example, logic instructions implementing the functionality of flow analyzer processing module 201, hematology analyzer data processing module 202, cross instrument analysis module 203, and data manager 216.

One or more memories 205 can be located on a single platform or can be distributed over multiple platforms. One or more memories 205 consist of dynamic memory components, including, for example, dynamic random access memory (DRAM), and static random access memory (SRAM). Memory 205 can be used for loading software program code and/or logic instructions to be executed, to hold intermediate processing data, and to hold the results of particle analysis before being stored in persistent storage devices 206 or 211, or otherwise disposed. Memory 205, for example, SRAM, can also be used for holding configuration parameters such as those useful in configuring hardware or software implemented logic and/or control the operation of flow cytometer 101 and hematology analyzer 102.

One or more persistent storage devices 206 can be located on a single platform or can be distributed over multiple platforms. Persistent storage devices 206 can include hard disk drives, DVD, Flash memory, or other computer-readable data storage media. Persistent storage devices 206 can be used for storing commands, scripts, software programs, test profiles, etc., that can be used for the operation of Flow-H 100 or one or more of its components. Persistent storage devices 206 can be used for intermediate data generated during processing of one or more components of Flow-H 100, and also to store results generated by flow cytometer 101, hematology analyzer 102, and the combined system. Persistent storage devices 206 can also store profiles and rules that are used in processing results from one or more components of Flow-H 100 such as flow cytometer 101 and/or hematology analyzer 102. Profiles, for example, can specify tests, and the type of interrogations and/or measurements to be performed in flow cytometer 101 and hematology analyzer 102. Rules, for example, can specify how cell populations can be identified and enumerated in a scatter plot and/or what parameters are to be measured or calculated for each cell population. One or more memories 205 and one or more persistent storage devices 206 collectively, can be considered persistent storage devices. A person of ordinary skill in the art would recognize that, in some embodiments, one or more memories 205 can be used also for holding and/or storing results from hematology analyzer 102 or flow cytometer 101.

In one embodiment, data manager 216 includes the functionality to store, organize, manage, and access data in Flow-H 100. The data handled by data manager 216 can include results data from flow cytometer 101, hematology analyzer 102, and the combined system. The data handled by data manager 216 can also include configuration parameters, and profiles and rules that are used for the operation of the system. For example, configuration data can include configuration parameters for flow cytometer 101, hematology analyzer 102, user interface 104, sample dispenser 105, and the combined system. Profiles and rules can be stored defining, for each type of test to be run, the configurations for the test and how the resulting event data and/or scatter plots are to be interpreted. In embodiments of the present invention, profiles and rules can be specified in one or more conventional scripting or programming languages, such as, for example, Perl, XML, Java, or C++, a hardware description language (HDL), or in a custom format. In one embodiment, data manager 216 includes the middleware component of a conventional lab information system. Data manager 216 can include a commercially available database management system, such as ORACLE DBMS available from ORACLE Corporation, or a custom data managing capability.

Flow interface 207 includes functionality to communicate between components of data processing system 103 and flow cytometer 101. For example, in embodiments where all or substantially all of the relevant flow cytometric data processing occurs in data processing system 103, flow interface 207 can include functionality to communicate with signal generation components of flow cytometer 101 and interpret such signals. In other embodiments where substantially all flow cytometer related processing occurs within flow cytometer 101, flow interface 207 can include functionality, for example, to enable the communication between the flow cytometer and the rest of Flow-H 100 to provide flow cytometer 101 with any additional data required. In yet other embodiments, flow interface 207 can provide a generic interface compatible with, and connecting to, one or more flow cytometers. For example, data processing system 103 can provide generic functionality that combines results according to the teachings in this disclosure, and is not restricted to one particular flow cytometer.

Hematology interface 208 includes functionality to communicate between components of data processing system 103 and hematology analyzer 102. For example, in embodiments where all or substantially all of the relevant hematology analysis data processing occurs in data processing system 103, hematology interface 208 can include functionality to communicate with signal generation components of hematology analyzer 102 and interpret such signals. In other embodiments where substantially all hematology analyzer related processing occurs within hematology analyzer 102, hematology interface 208 can include functionality, for example, to enable the communication between the hematology analyzer and the rest of Flow-H 100 to provide hematology analyzer 102 with any additional data required for processing its data. In yet other embodiments, hematology interface 208 can provide a generic interface compatible with, and connecting to, one or more hematology analyzers. For example, data processing system 103 can provide generic functionality that combines results according to the teachings in this disclosure, and is not restricted to one particular hematology analyzer.

In one embodiment, output interface 209 includes functionality to accept results data and any other information that flows from data processing system 103 to user interface 104. For example, output module 209 can include processing performed on the results data before being displayed on display 210, such as formatting a scatter plot for display 210.

Flow cytometer data processing module 201 includes flow cytometer specific data processing. In one embodiment, for example, flow cytometer data processing module 201 includes functionality to interpret optical and electrical signals generated by the particle measurement modules of flow cytometer 101 as cells are interrogated in the flow chamber, processing of the data to refine and/or enhance the data, and perform some or all of a predetermined analysis of populations. Flow cytometer data processing module 201 can be distributed among multiple platforms, including, for example, flow cytometer 101 and data processing module 103.

Hematology analyzer data processing module 202 includes hematology analyzer specific data processing. In one embodiment, for example, hematology analyzer data processing module 201 includes functionality to interpret optical and electrical signals generated by the particle measurement modules of hematology analyzer 102 as cells arc interrogated, processing of the data to refine and/or enhance the data, and perform some or all of a predetermined analysis of populations. Hematology analyzer data processing module 202 can be distributed among multiple platforms, including, for example, hematology analyzer 101 and data processing module 103.

Cross-instrument analysis processing module 203 includes the functionality to analyze results from flow cytometer 101 and hematology analyzer 102, in combination. For example, processing in this module enables the use of results generated by hematology analyzer 102 and hematology analyzer data processing module 201 in resolving cell populations appearing in results from flow cytometer 101 and flow cytometer data processing module 201. Details of the methods involved in this processing are described below with respect to FIGS. 3 and 4.

Communication device 212 interconnects components of data processing system 103 to each other, and can include one or more communications mediums, including but not limited to a peripheral component interconnect (PCI) bus or Extended Industry Standard Architecture (EISA) bus.

The processing logic of components of Flow-H 100, including cross-instrument analysis processing module 103 and data manager module 216, can be implemented in hardware, software, or in any combination thereof. For example, a computer program product implementing the functionality of one or more components 201, 202, 203, and 216, can include logic instructions specified in one or more programming languages such as C, C++, Assembly, Java, or HDL.

Method for Cross-Instrument Pattern Analysis for Cell Population Discrimination

Figure 3:
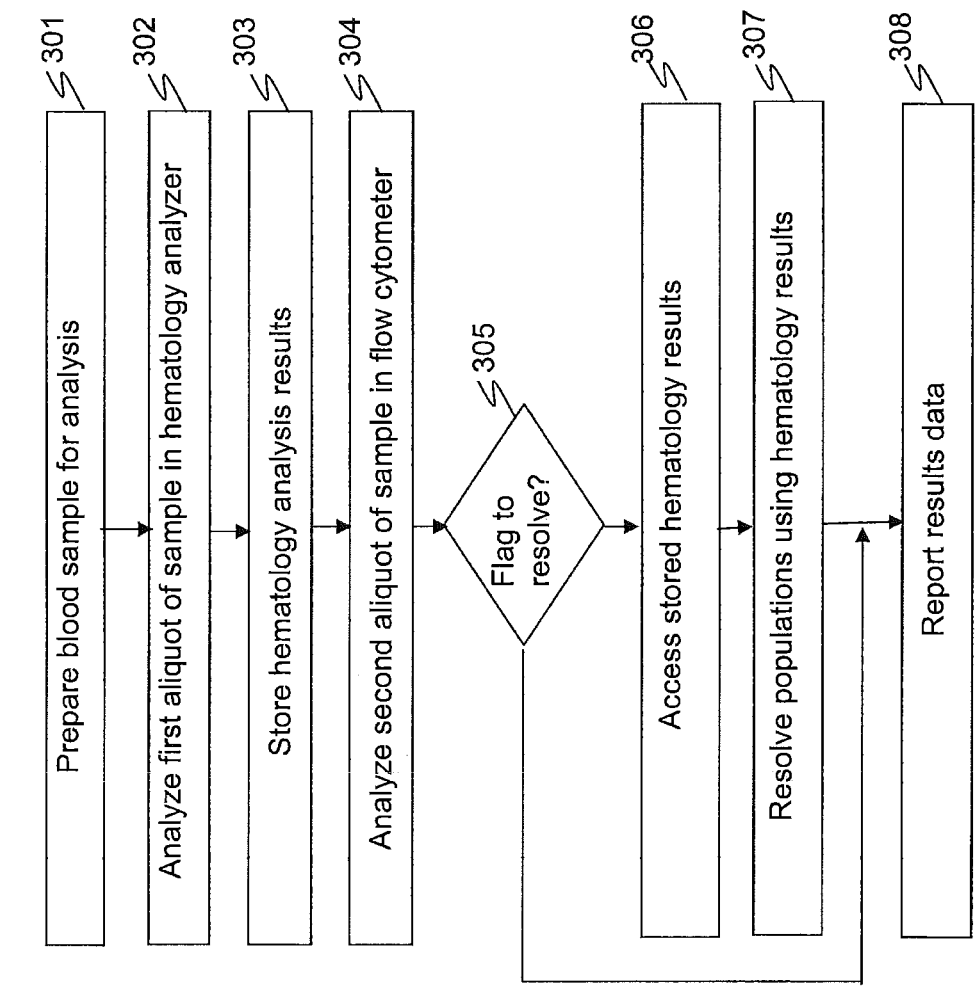
FIG. 3 illustrates a process for combining results from a hematology analyzer and a flow cytometer, according to an embodiment of the present invention.

FIG. 3 illustrates a process 300 having steps 301-308 for automatically combining the results of a flow cytometer and a hematology analyzer, according to an embodiment of the present invention. Process 300 illustrates the method of analysis for one blood sample in Flow-H 100. However, a person skilled in the art would recognize that process 300 can be performed repetitively to automate the analysis of multiple samples.

In step 301, a blood sample is prepared for analysis in Flow-H 100. In one embodiment, for example, where Flow-H 100 does not include an automated sample dispenser, step 301 can include preparing two aliquots of the same blood sample—one for analysis in hematology analyzer 102 and the other for analysis in flow cytometer 101. An operator can manually dispense the first aliquot to hematology analyzer 102, and the second aliquot into flow cytometer 101. In another embodiment, for example, where Flow-H 100 includes an automated sample dispenser such as sample dispenser 105, depending on the sample preparation capabilities of sample preparation device 105, multiple samples can be queued for processing in Flow-H 100. For example, in some embodiments, sample dispenser 105 automatically divides a blood sample into two aliquots. Based on pre-specified (or preprogrammed) instructions, sample dispenser 105 can also prepare one aliquot to be analyzed in hematology analyzer 102 for a group of hematology tests, and prepare the second aliquot to be analyzed in flow cytometer 101 for a second group of flow cytometry tests. It should be noted that embodiments of the present invention encompass Flow-H 100 devices with sample dispensers having varied capability levels, for example, from only very basic sample dispensing, to fully automated sample preparation and dispensing. Embodiments can also include Flow-H devices that do not have an integrated sample dispenser.

Some embodiments of the present invention can use an identification associated with each sample, for example, a unique barcode, to automate processing and to associate the processing of the same sample in hematology analyzer 102 and flow cytometer 101. For example, in step 301, at sample preparation stage, bar code device 107 can stamp each sample with a unique barcode associated with preprogrammed patient information and/or test requirements. Patient information, sample information, and test instructions that should be performed for each patient, for example, can be associated with a unique code such as a barcode and stored in a persistent storage device, such as persistent storage device 206, to be accessed during the processing of the corresponding sample. Other known identification indicia can be used, as would be apparent to a person of ordinary skill in the arts, such as laser etching, nano particle tagging, or the like.

Persons of skill in the art would be familiar with the process of preparing a blood sample for analysis in a hematology analyzer, as well as the process of preparing a sample for analysis in a flow cytometer. They would also recognize that the preparation process can differ based on the tests to be executed on that sample.

In step 302, a first aliquot of the sample prepared in step 301 is introduced into a hematology analyzer, such as hematology analyzer 102, for analysis. The aliquot is then analyzed in hematology analyzer 102 based on the requirements of one or more prespecified tests. In some embodiments, as each aliquot is introduced into hematology analyzer 102, based on the barcode, or other indicia or tag, associated with that aliquot, the testing requirements can be looked up and any configuration adjustments required for the particular tests can be made to hematology analyzer 102 prior to the analysis of that aliquot. In other embodiments, aliquots of samples can be introduced to hematology analyzer 102 by ordering them according to the types of tests to be run, so that configuration adjustments to the hematology analyzer 102 are minimized and/or any such adjustments can be manually performed only when required.

The process of measuring properties of a cell sample within hematology analyzer 102 is generally well known in the art. In one embodiment, as cells of the cell sample flow through a measurement region, electrical and/or optical sensors are used to interrogate the sample based on various test requirements, for example, such as the types of measurements required for the test being run as specified in an associated profile. Example interrogation technology, such as those using electrical impedance and VCS technology are described above. The electrical and/or optical signals that are generated in response to the interrogation are then converted into corresponding data. The data can also be pre-processed to enhance its accuracy, for example, by eliminating and/or reducing effects of signal abnormalities and stray data points.

The data generated in the hematology analyzer 102 is then subjected to analysis according to various test requirements. For example, a profile associated with the test being run on the sample can include rules specifying requirements such as location boundaries on a scatter plot for one or more cell populations to be identified. The analysis of the data can take place in or out of hematology analyzer 102. For example, analysis of the data from hematology analyzer 102 can be performed using hematology analyzer data processing module 202 in data processing device 103. Event data generated from hematology analysis is generally analyzed to determine cell counts and/or populations. Specific measurement and analysis methods differ according to the requirements of the tests being performed. In general, the events representing the cells are mapped on a scatter plot and a definitive separation between cell clusters on the scatter plot is algorithmically determined. Cell populations can be enumerated (i.e., particularly identified) when it is in an area that does not substantially overlap the area of another cell population. If two cell populations overlap, or are otherwise indistinguishable, the results may be skewed or inconclusive. An unresolved population is a cell population that is not clearly distinguishable. An example analysis of event data is described below.

In step 303, the hematology results, i.e., results generated by performing hematology analysis on the blood sample, are stored, for example, in persistent storage devices 206. The stored hematology results should be accessible, preferably, based on criteria such as, sample identification, type of test, and type of cell population. The hematology results can be stored using data manager 216. Data manager 216, as described above, can include a database management system that enables data to be stored and indexed according to predetermined criteria, such that the entire data of a blood sample, or parts of it can be searched for and accessed efficiently.

In step 304, a second aliquot from the same blood sample as the first aliquot that was analyzed in hematology analyzer 102, is introduced into flow cytometer 101. As described above with respect to introducing a sample into hematology analyzer 102, the second aliquot of the sample can be introduced to flow cytometer 101 either manually or using an automated sample dispenser, such as, for example, sample dispenser 105. Also, as described above, prior to introducing the second aliquot into flow cytometer 101, it should have been appropriately prepared for flow cytometric analysis. The preparation requirements can include the introduction of one or more dyes or fluorochromes into the sample, a lysing process, and an incubation process, depending on the type of tests to be executed. Similar to the preparation of samples for introducing to hematology analyzer 102, the preparation process can include manual as well as automated processing.

Step 304 includes the measurement of the second aliquot of the cell sample within flow cytometer 101. In some embodiments, as each aliquot is introduced into flow cytometer 101, based on the barcode associated with that aliquot the testing requirements are looked up and any configuration adjustments required for the particular tests can be made to flow cytometer 101 prior to the measurement of that aliquot. In other embodiments, aliquots of samples can be introduced to flow cytometer 101 by ordering them according to the types of tests to be run, so that configuration adjustments to the flow cytometer 101 are minimized and/or any such adjustments can be manually performed only when required.

The process of interrogation of the cell sample within flow cytometer 101 is generally well known in the art. As a cell sample that has been mixed with a set of fluorochromes flow through a measurement region electrical and/or optical sensors are used to interrogate the sample based on various test requirements, for example, such as the types of measurements required for the test being run as specified in an associated profile. Example interrogation technologies, such as those using electrical impedance, VCS, detection of the scatter of light of various wavelengths were described above. The electrical and/or optical signals that are generated in response to the interrogation are then converted into corresponding data. The data can also be pre-processed to enhance its accuracy, for example, by eliminating and/or reducing effects of signal abnormalities.

The data generated by flow cytometer 101 is then subjected to analysis according to various test requirements. For example, a profile associated with the test being run on the sample can include rules specifying requirements such as location boundaries on a scatter plot for one or more cell populations to be identified. The analysis of the data can take place within or external to flow cytometer 101. For example, analysis of the data from flow cytometer 101 can be performed using flow cytometer data processing module 201 in data processing device 103. Event data generated from flow cytometer analysis is generally analyzed to determine cell counts and/or populations. Specific measurement and analysis methods differ according to the requirements of the tests being performed. An exemplary analysis of event data generated by flow cytometric analysis is described below.

In step 305, as the data from flow cytometer 101 is being analyzed, one or more flags can be raised based on predetermined criteria. Flags can be used to communicate information from one processing module or component to another. Flags can be implemented in one or more means such as, a software-generated message, a hardware signal, or a value written to memory or a file. For example, cell populations that cannot be conclusively resolved using only the data from flow cytometer can cause the generation of one or more such flags. In one embodiment, preprogrammed profiles and/or rules can be used in the analysis of the flow cytometry results to identify unresolved populations on which to generate a flag, and to identify means by which such unresolved populations can be resolved. An example where a cell population cannot be conclusively resolved using only flow cytometry results is described below with respect to FIGS. 5-6.

If one or more flags are raised in step 305, then in step 306, stored hematology results are accessed automatically to obtain the data required for responding to said flag or flags. In one embodiment, each unresolved cell population and other relevant blood sample criteria can be matched against one or more preprogrammed profiles and/or rules to determine the data required from hematology results. Hematology results for the same sample are then retrieved, for example, using the services of data manager 216, to determine any needed information to resolve the one or more unresolved cell populations.

Then in step 307, the hematology results accessed in step 306 are used to resolve the one or more unresolved cell populations determined in flow cytometric analysis in step 304. The search for, and the analysis of, the corresponding hematology results can be aided by a preprogrammed profile and/or rules retrieved based on one or more criteria such as, the characteristics of the cell sample, the tests being executed, and the unresolved populations. In one embodiment, the processing involved in step 307 can be performed in cross-instrument analysis processing module 203, and the processing involved in steps 304-306 can be performed by flow cytometer data processing module 201, data manager 216, and cross-instrument analysis processing module 203.

In step 308, result data can be reported. For example, the reporting can be to a display or other output device, such as, for example, user interface 104. The result or results data reported can include hematology results, flow cytometric results, and/or any combined results. Step 308 can also include a saving of the flow cytometric results and/or the combined results in a persistent storage device, such as persistent storage device 206. In one embodiment, the processing involved in step 308 can be performed by output module 209 and data manager 216.

If, in step 305, it is determined that flow cytometric analysis generated no flags requiring the retrieval of corresponding hematology results, then processing proceeds directly to step 308.

Figure 4:
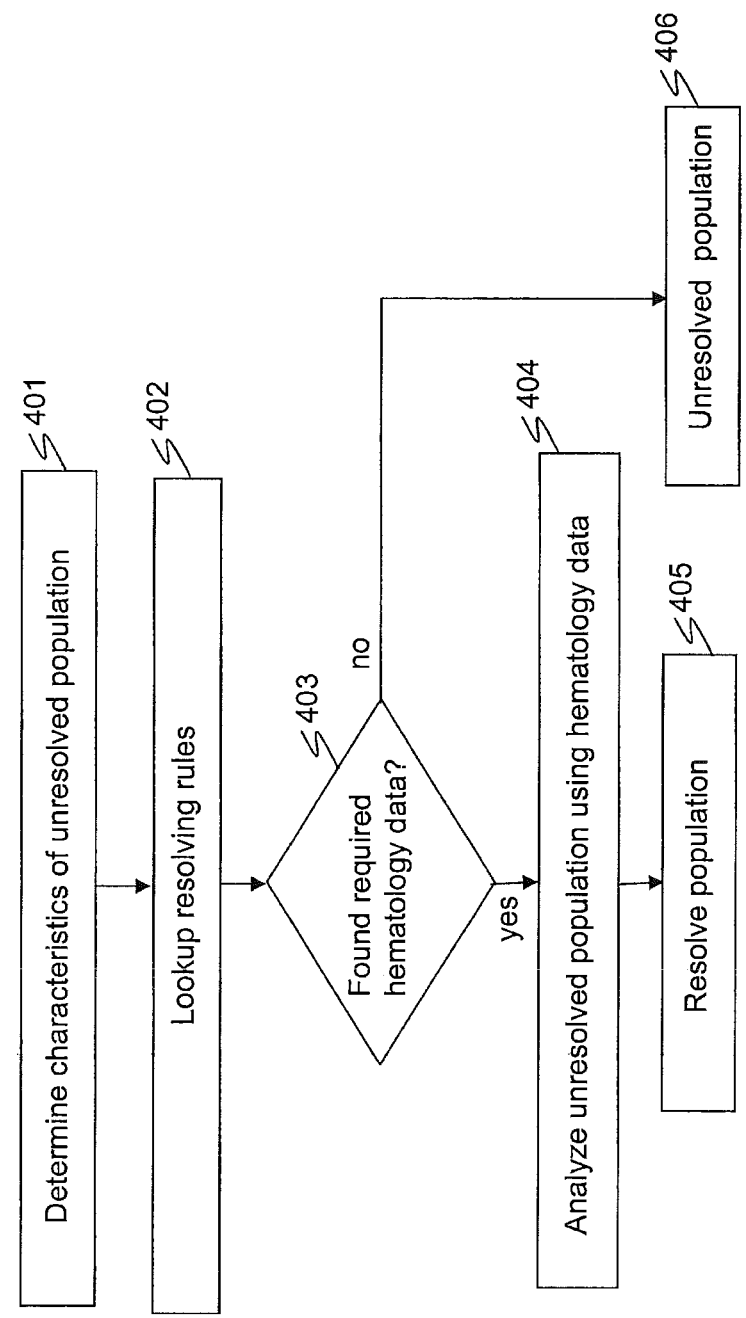
FIG. 4 illustrates details of the resolve step of FIG. 3, according to an embodiment of the present invention.

FIG. 4 provides a more granular view of the processing in step 307, according to one embodiment of the present invention. In step 401, characteristics of any unresolved populations can be determined by, for example, matching flow cytometric results against a preprogrammed profile of the test being run. The profile and/or rules associated with the profile can detect unresolved cell populations and/or any other cell populations that require further resolution using hematology results. For example, each type of test can have one or more preprogrammed profiles stored in persistent storage device 206 that can be accessed using data manager 216. The profiles and/or rules associated with the profiles can specify characteristics of the cell population that are to be expected, for example, based on location of the cell event data on a scatter graph. For example, a preprogrammed profile for a test-A can specify that any cell events appearing in area-1 of a scatter plot are type-A cells, any cells in area-2 are type-B cells, etc. A rule associated with the profile can specify that if more than 10% of the cell events appear in area-3 and certain other criteria are met, then the cell population in area-3 is unresolved and further analysis using hematology results for the corresponding blood sample is required.

In step 402, one or more preprogrammed rules for resolving the unresolved population are determined. For example, a profile associated with the type of test being executed can have associated rules, and the applicable rules can be determined based on the characteristics of the unresolved cell population such as, corresponding event locations on a scatter graph. One such rule can specify that the data corresponding to a particular test should be retrieved from the corresponding hematology results.

In step 403, the corresponding hematology results are obtained based on the type of test and/or more granular characteristics such as the particular test results being sought. If the necessary hematology results are not found, then the unresolved population determined in step 401 remains unresolved (and can subsequently be reported out as unresolved).

If the hematology results required for resolving the cell population are located, then, in step 404, those hematology results are analyzed to determine how the particular unresolved populations in the flow cytometric data is to be resolved. For example, preprogrammed rules can specify that, if corresponding hematology results match a profile with specified characteristics then the unresolved population should be resolved in a particular manner. Accordingly, in step 404, the unresolved population in flow cytometric results is resolved using the corresponding hematology results.

Process 300, as should be clear to persons of skill in the art, can be adapted to be used for batch mode processing of blood samples or other bodily samples in Flow-H 100. Process 300 can be adapted to resolve flow cytometric data in real-time (as described) or to resolve such unresolved cell population in a post-processing step after the completion of flow cytometric analysis. In the first instance, hematology results are required when the flow cytometric analysis is executed. In the second instance, the order of the generation of hematology results and the flow cytometric results can not be determinative. In other embodiments, process 300 can also be adapted such that additional tests are automatically triggered when data processing module 103 determines that additional results are required to resolve certain cell populations. For example, in one embodiment, hematology analysis of a sample can be triggered only when flow cytometric analysis of the corresponding sample includes a cell population that cannot be conclusively determined.

Example Embodiments

Myeloblasts are the most immature granulocytic cells in blood, typically found in bone marrow. Enumerating blast cells, and in particular enumerating Myeloblasts, are important in the diagnosis and treatment of several diseases such as acute leukemia. Automated hematology analyzers, such as the COULTER® LH 700 series manufactured by Beckman Coulter, or XE-2100 manufactured by Sysmex, do not have the capability of Myeloblast enumeration. When Myeloblasts are found to be potentially present in a sample being analyzed, conventional hematology analyzers such as the COULTER® LH 700 and XE-2100 only display messages indicating to the user that there is a potential presence of Myeloblasts. Thereafter, in order to confirm or reject the presence of Myeloblasts in the sample, a laboratory technologist may manually analyze each of the samples that caused display messages indicating the potential presence of Myeloblasts.

Figure 5:
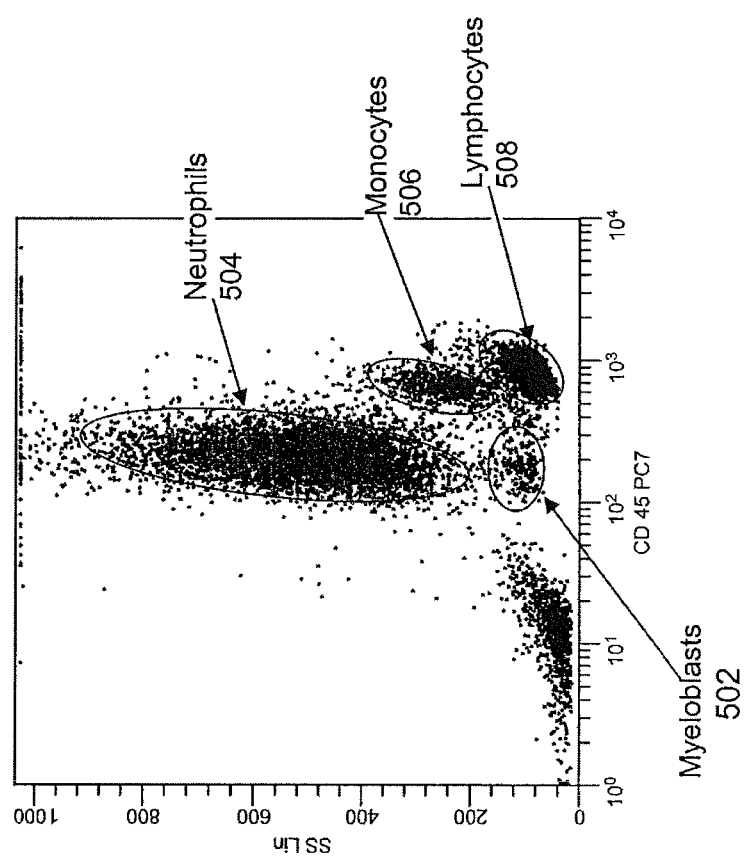
FIG. 5 is a scatter plot of Myeloblast-positive blood sample analyzed in a flow cytometer, according to an embodiment of the present invention.

Flow-cytometry instruments like the FC 500™ manufactured by Beckman Coulter, or FACSCanto™ manufactured by Becton Dickinson, can enumerate Myeloblasts using an antibody such as CD45 and side-scatter. Myeloblasts usually have similar side scatter values as Lymphocytes or Monocytes, and similar or lower CD45 expression as Neutrophils. FIG. 5 shows a scatter plot of a Myeloblast-positive sample analyzed in a flow cytometer, with populations of Myeloblasts 502, Neutrophils 504, Monocytes 506, and Lymphocytes 508 indicated.

Figure 6:
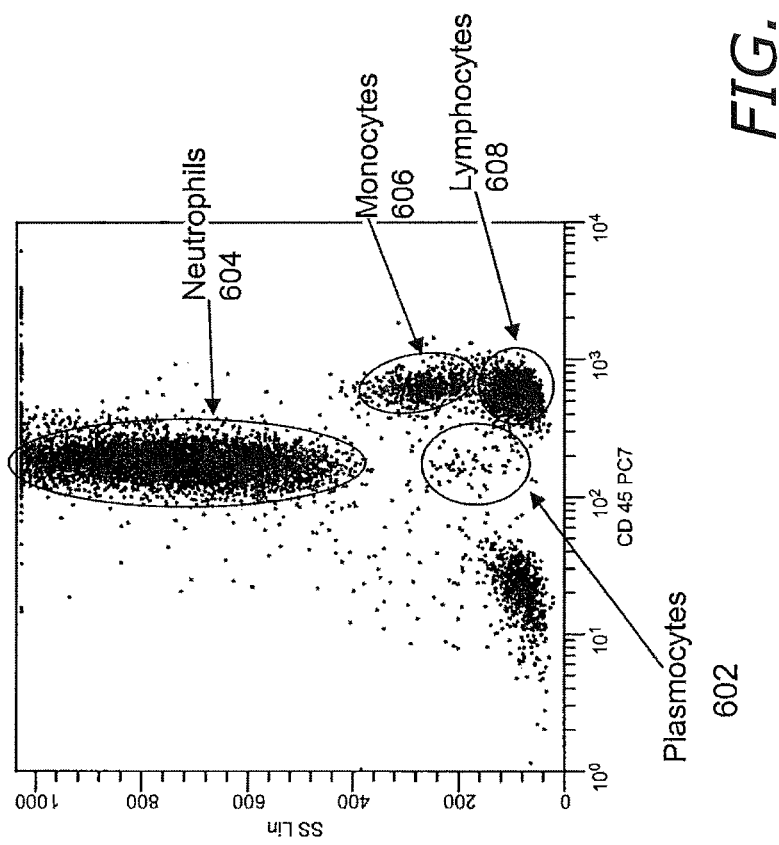
FIG. 6 is a scatter plot of Plasmocyte-positive blood sample of FIG. 5 analyzed in a flow cytometer, according to an embodiment of the present invention.

However, the flow-cytometric method of Myeloblast enumeration using side scatter and CD45 can be falsely elevated if the sample includes Plasmocytes because the Plasmocytes appear in the same location as blast cells in a scatter plot. Plasmocytes are antibody producing white blood cells, and have different biological significance than Myeloblasts. FIG. 6 shows scatter plot of a Plasmocyte-positive sample analyzed in a flow cytometer with populations of Plasmocytes 602, Neutrophils 604, Monocytes 606, and Lymphocytes 608 indicated. It can be seen that the location of Myeloblasts 502 substantially overlaps with the location of Plasmocytes 602.

Figure 7:
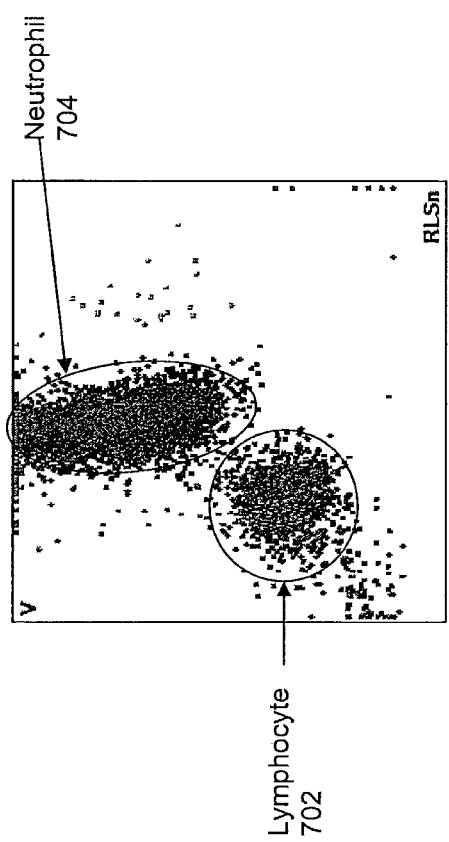
FIG. 7 is a scatter plot of Myeloblast-positive blood sample of FIG. 5 analyzed in a hematology analyzer, according to an embodiment of the present invention.
Figure 8:
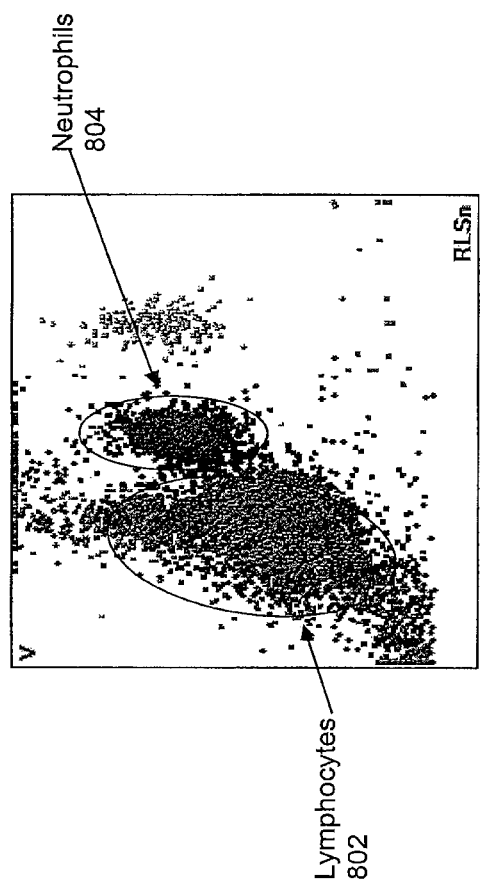
FIG. 8 is a scatter plot of Plasmocyte-positive blood sample of FIG. 6 analyzed in a hematology analyzer, according to an embodiment of the present invention.

Despite being incapable of enumerating Myeloblasts, automated hematology analyzers produce patterns indicative of the presence of Myeloblasts and/or Plasmocytcs in analyzed samples. Examples of such patterns indicative of Myeloblasts and/or Plasmocytes are shown in FIGS. 7-8. FIG. 7 shows a scatter plot of a Myeloblast-positive sample from hematology analysis data, and FIG. 8 shows a scatter plot of a Plasmocyte-positive sample from hematology analysis data. The Neutrophil population distribution 704 is substantially elongated in the volume (V) direction, while the Lymphocyte population 702 is not substantially elongated in the Myeloblast-positive sample of FIG. 7. The Lymphocyte population distribution 802 is substantially elongated in the volume (V) direction, while the Neutrophil population 804 is not substantially elongated in the Plasmocyte-positive sample of FIG. 8.

Therefore, in one embodiment, the present invention automatically retrieves the corresponding hematology analysis data to determine the characteristics of the Neutrophil population and the Lymphocyte population, when it detects a population (as shown in FIGS. 5-6) in flow cytometric data that could either be Myeloblasts or Plasmocytes. If the Neutrophil population distribution is substantially elongated in the volume direction and the Lymphocyte population is not substantially elongated, then the unresolved population in the flow cytometric data is determined to be Myeloblasts. If the Lymphocyte population is substantially elongated and the Neutrophil population is not substantially elongated in the volume direction, then the unresolved population in the flow cytometric data is determined to be Plasmocytes.

For example, when analyzing a blood sample, in steps 302 and 303, Flow-H 100 can analyze and store hematology results such as that shown in FIG. 7 or FIG. 8. When analyzing the corresponding sample in steps 304-305, Flow-H 100 can detect a population in the location where Mycloblasts or Plasmocytcs appear, as shown in FIGS. 5 and 6, and generate a flag to indicate an unresolved population. In steps 306-307, Flow-H 100 accesses the previously stored hematology analysis data and determines one or more characteristics of the Lymphocyte population distribution and/or the Neutrophil population distribution. For example, comparing a characteristic such as the standard deviation of a population distribution with a threshold can indicate whether the distribution is elongated in the volume direction. Flow-H 100 can have preprogrammed profiles and/or rules that allow the algorithmic matching of the flow cytometric data to a scatter plot having an unresolved population such as Myeloblasts in this example. Preprogrammed profiles and/or rules can also specify the type of data required to resolve the unresolved population, such as, in this example, that Lymphocyte and/or Neutrophil characteristics in hematology data is required.

Another example embodiment is illustrated in relation to FIGS. 9-14. In some applications it is important to distinguish between populations of immature granulocytes, eosinophils and neutrophils in white blood cells. The presence of immature granulocytes in blood is generally useful for detecting abnormal bone marrow activity. Immature granulocytes are also useful in the detection of certain stages of leukemia. The elevation or decrease of eosinophils and/or neutrophils populations can be indicative of other diseases. For example, eosinophils are generally indicative of allergic reactions and neutrophils can indicate bacterial infections.

Figure 9:
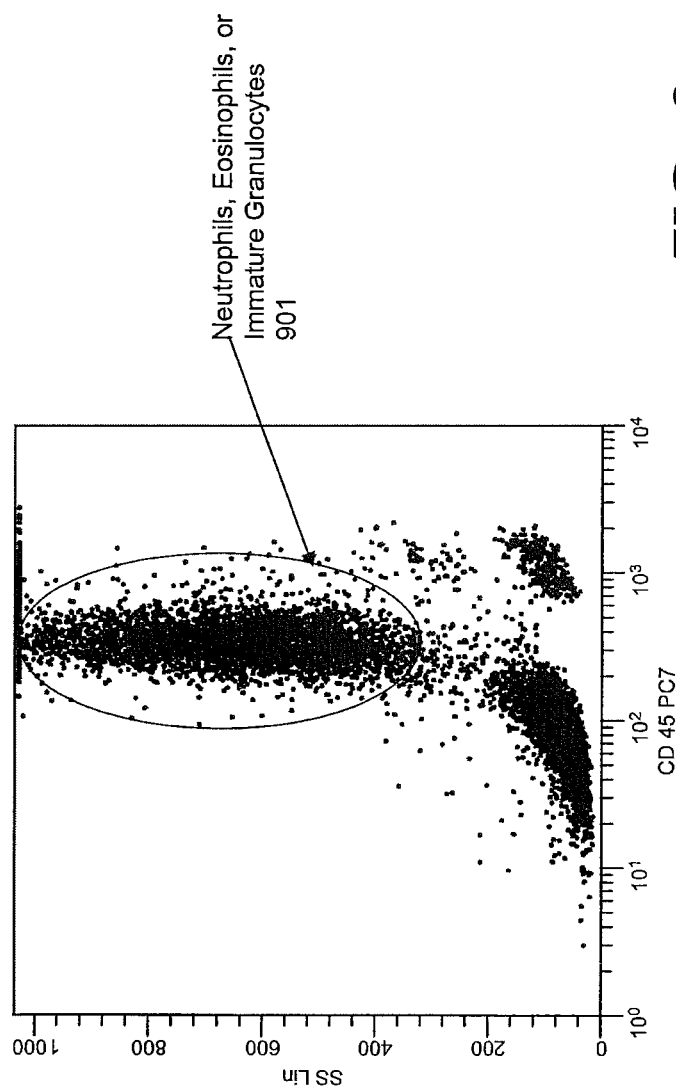
FIG. 9 is a scatter plot of a immature granulocyte-positive sample analyzed in a flow cytometer.
Figure 10:
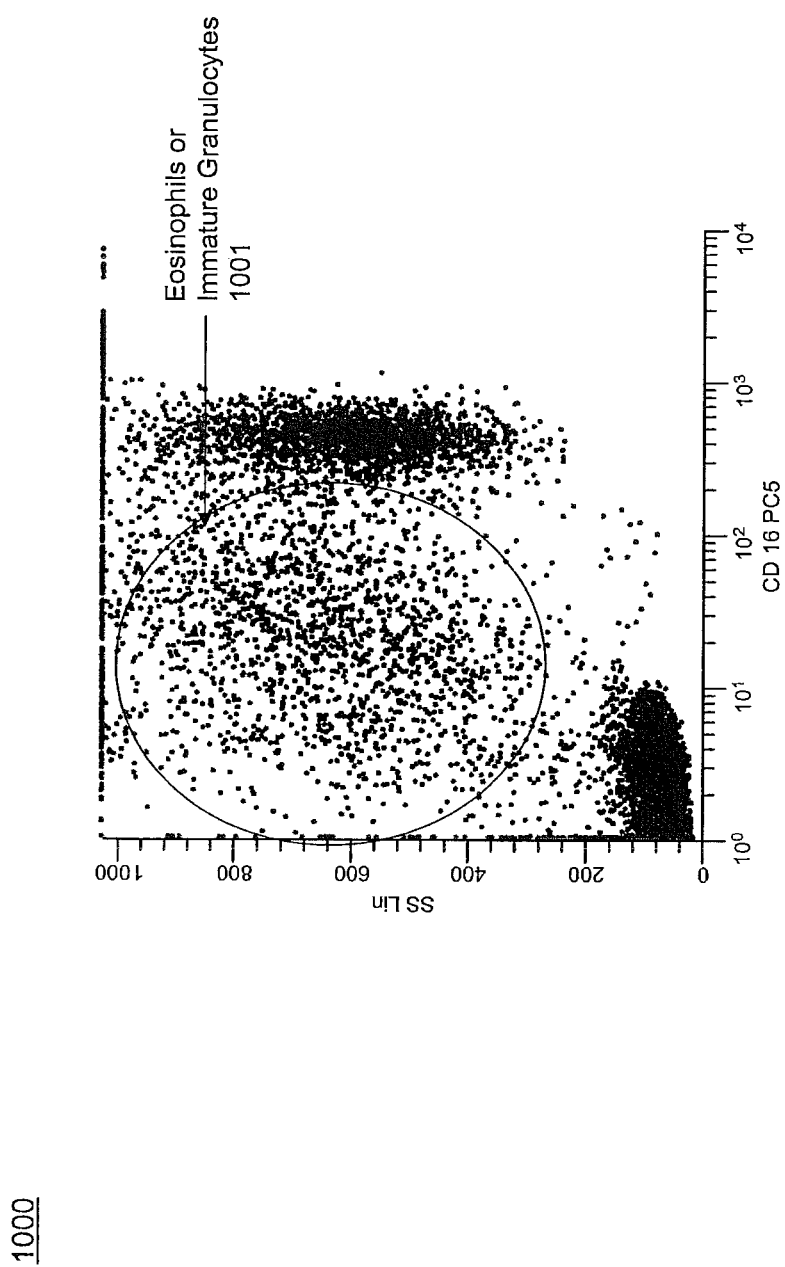
FIG. 10 is a scatter plot of a immature granulocyte-positive sample analyzed in a flow cytometer.
Figure 11:
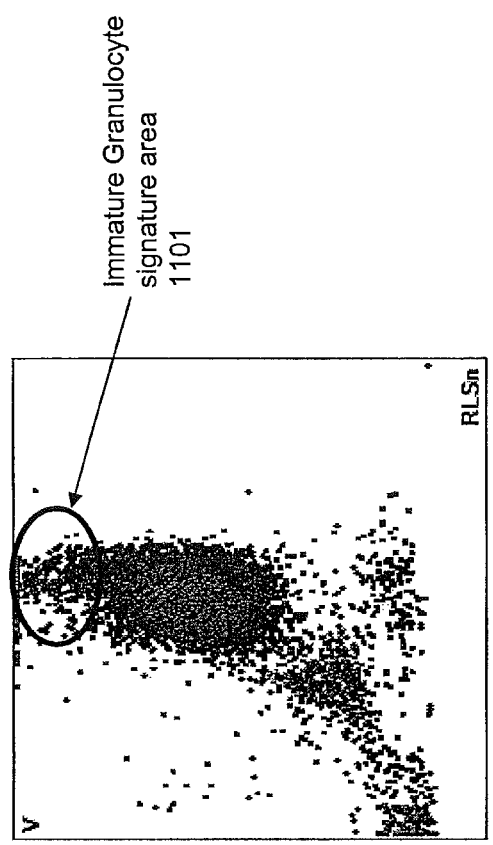
FIG. 11 is a scatter plot of a immature granulocyte-positive sample of FIGS. 9 and 10 analyzed in a hematology analyzer.

FIGS. 9 and 10 show a scatter plots 900 and 1000, respectively, of a WBC sample with immature granulocytes generated using a flow cytometer. Scatter plot 900 shows side scatter when antibody CD45 is used with the sample, and scatter plot 1000 shows side scatter when antibody CD16 is used with the same sample. As shown in scatter plots 900 and 1000, the results generated by a flow cytometer are not sufficient to distinguish between immature granulocytes and eosinophils. For example, population 901 can include one or more populations of neutrophils, eosinophils, and immature granulocytes. Population 1001 can include populations of either eosinophils or immature granulocytes. However, when the same sample is submitted for hematology analysis, a distinct immature granulocyte population can be identified based on a signature pattern in the resulting scatter plot. For example, scatter plot 1100 in FIG. 11 plots volume measurements and light scatter (rotated light scatter) from a hematology analyzer for the same sample having immature granulocytes. Population 1101 distinctively identifies immature granulocytes.

Figure 12:
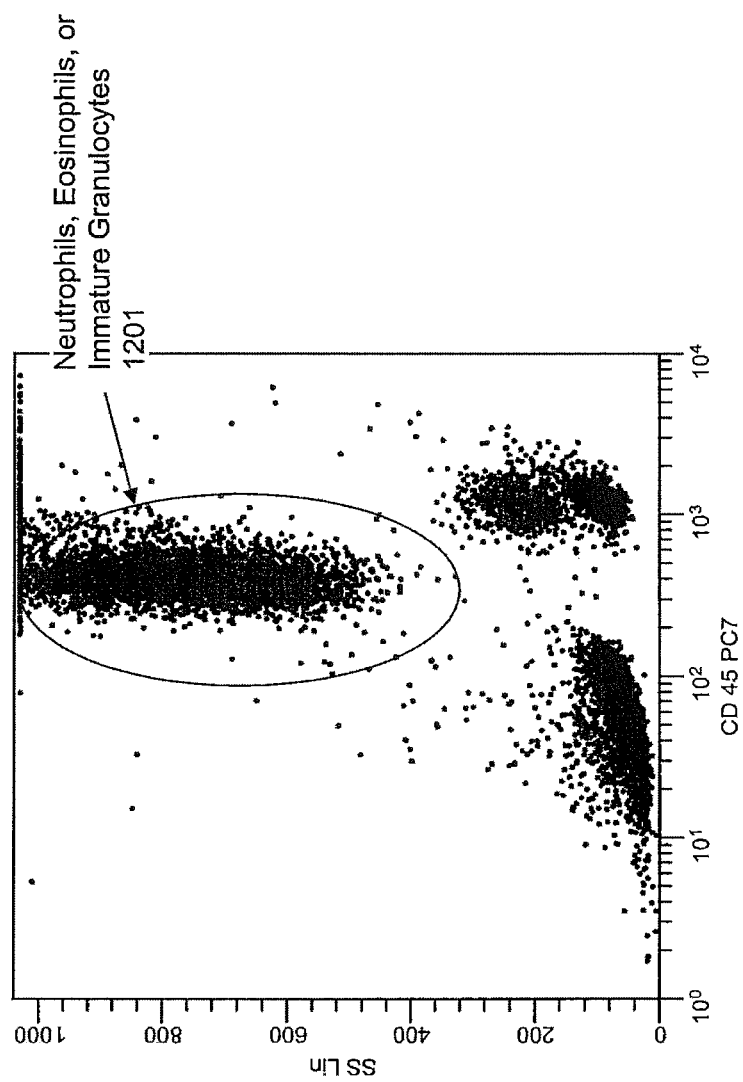
FIG. 12 is a scatter plot of a eosinophil-positive sample analyzed in a flow cytometer.
Figure 13:
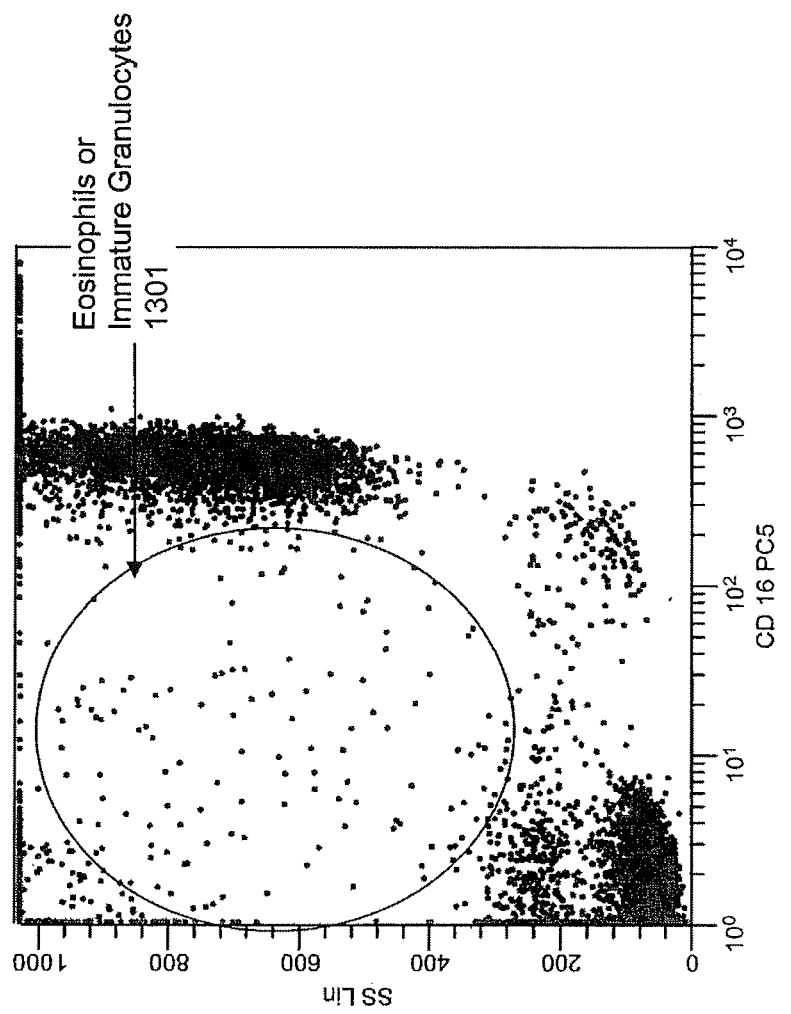
FIG. 13 is a scatter plot of a eosinophil-positive sample analyzed in a flow cytometer.

FIGS. 12-13 show scatter plots 1200 and 1300, where a eosinophil-positive blood sample (blood sample with an elevated eosinophil level) is analyzed using a flow cytometer. Scatter plot 1200 shows side scatter when antibody CD45 is used with the sample, and scatter plot 1300 shows side scatter when antibody CD16 is used with the same sample. As shown in scatter plots 1200 and 1300, the results generated by a flow cytometer are not sufficient to distinguish between immature granulocytes and eosinophils. For example, population 1201 (as was the case with population 901 above) can include one or more populations of neutrophils, eosinophils, and immature granulocytes. Population 1301 (as was the case with population 1101 above) can include populations of either eosinophils or immature granulocytes. However, when the same sample is submitted for hematology analysis, a distinct eosinophil population can be identified based on a signature pattern in the resulting scatter plot. For example, scatter plot 1400 in FIG. 14 plots volume measurements and light scatter (specifically, rotated light scatter) from a hematology analyzer for the same eosinophil-positive blood sample. Population 1401 distinctively identifies the eosinophil population. As described in relation to the Myeloblast example above, Flow-H 100 can be configured to automatically resort to hematology analysis results to resolve populations (for example, as shown in scatter plots 1100 and 1400) when flow cytometry analysis yields populations such as 901, 1001, 1201 or 1301.

In this disclosure, methods and systems are disclosed that can improve the efficiency and accuracy of particle analysis, including blood sample analysis, through combining the power and functionality of different particle analyzers such as a hematology analyzer and a flow cytometer. The disclosed methods and systems yield substantial improvements over current methods and systems. Persons skilled in the art will understand that the techniques disclosed herein can be applicable a number of biological or industrial particles and is also applicable to a number of detection methods using electrical, optical or acoustic mediums.

The foregoing description of the invention has been presented for purposes of illustration and description. It is not intended to be exhaustive or to limit the invention to the precise form disclosed, and other modifications and variations may be possible in light of the above teachings The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A system for analysis of a blood cell suspension sample, comprising:
    a first particle analyzer configured to receive a first aliquot of the blood cell suspension sample as input and to produce a first data using a fluorescence measurement device, the first data including a cell population of a first cell type;
    a second particle analyzer configured to receive a second aliquot of the sample as input and to produce a second data using at least one of a cell volume measurement device, a light scatter measurement device, and a cell conductivity measurement device; and
    a computer comprising:
        memory having instructions stored thereon; and
        a processor associated with the memory, wherein the instructions cause the processor to:
            receive the first data and the second data;
            determine if there is substantial overlap in location of the first cell type and a second cell type in a plot of the first data where the substantial overlap is indicative of an inconclusive cell population;
            determine if there is substantial overlap in location of the first cell type and the second cell type in a plot of the second data; and
            when there is substantial overlap, automatically resolve the inconclusive cell population created by the substantial overlap in the first data using the second data to generate a resolved cell distribution wherein the computer identifies a signature pattern in the second data indicative of the presence of cells of the first cell type to determine if cells of the first cell type are present in the cell population.

2. The system of claim 1, further comprising:
    a reporting device configured to receive the resolved cell distribution from the computer and output the resolved cell distribution to a user interface.

3. The system of claim 1, wherein the first particle analyzer and the second particle analyzer are independent of each other and the first particle analyzer and the second particle analyzer simultaneously analyze cell suspension samples.

4. The system of claim 1, wherein the first particle analyzer is a flow cytometer and the second particle analyzer is a hematology analyzer.

5. The system of claim 1, wherein a T-blast cell population or a basophil cell population cause the substantial overlap.

6. The system of claim 1, wherein an eosinophil cell population or an immature granulocyte cell population cause the substantial overlap.

7. The system of claim 1, wherein the processor uses the second data to generate a scatter plot of volume versus light scatter.

8. The system of claim 7, wherein the light scatter is rotated light scatter.

9. The system of claim 1, wherein a myeloblast cell population or a plasmocyte cell population cause the substantial overlap.

10. The system of claim 1, wherein the cells of the first cell type cannot be enumerated in the second data.

11. The system of claim 1, wherein the signature pattern relates to a measurement of population mean and standard deviation.

12. The system of claim 1, wherein the signature pattern comprises a population distribution of data from a third cell type.

13. The system of claim 10, wherein the processor uses the first data to enumerate the cells of the first cell type.

* * * * *